(12) United States Patent
Ma et al.

(10) Patent No.: US 9,701,601 B2
(45) Date of Patent: Jul. 11, 2017

(54) OPTICALLY ACTIVE AXIALLY CHIRAL ALPHA-ALLENIC ALCOHOL, SYNTHESIS METHOD AND USE THEREOF

(71) Applicant: SHANGHAI INSTITUTE OF ORGANIC CHEMISTRY, CHINESE ACADEMY OF SCIENCES, Shanghai (CN)

(72) Inventors: Shengming Ma, Shanghai (CN); Juntao Ye, Shanghai (CN)

(73) Assignee: SHANGHAI INSTITUTE OF ORGANIC CHEMISTRY, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 14/401,051

(22) PCT Filed: Nov. 20, 2012

(86) PCT No.: PCT/CN2012/084896
§ 371 (c)(1),
(2) Date: Nov. 13, 2014

(87) PCT Pub. No.: WO2013/185435
PCT Pub. Date: Dec. 19, 2013

(65) Prior Publication Data
US 2015/0105567 A1    Apr. 16, 2015

(30) Foreign Application Priority Data
Jun. 12, 2012 (CN) .......................... 2012 1 0193176

(51) Int. Cl.
| | | |
|---|---|---|
| C07C 29/17 | (2006.01) | |
| C07C 311/16 | (2006.01) | |
| C07C 33/03 | (2006.01) | |
| C07C 33/12 | (2006.01) | |
| C07C 67/343 | (2006.01) | |
| C07C 29/00 | (2006.01) | |
| C07D 307/30 | (2006.01) | |
| C07D 307/28 | (2006.01) | |
| C07C 33/14 | (2006.01) | |

(52) U.S. Cl.
CPC .............. *C07C 29/17* (2013.01); *C07C 29/00* (2013.01); *C07C 33/03* (2013.01); *C07C 33/12* (2013.01); *C07C 33/14* (2013.01); *C07C 67/343* (2013.01); *C07C 311/16* (2013.01); *C07D 307/28* (2013.01); *C07D 307/30* (2013.01); *C07B 2200/07* (2013.01); *C07C 2101/08* (2013.01); *C07C 2101/14* (2013.01)

(58) Field of Classification Search
CPC ..... C07C 311/16; C07C 29/00; C07C 67/343; C07C 2101/14; C07C 2101/08; C07D 307/30; C07B 2200/07

USPC .......................................................... 549/507
See application file for complete search history.

(56) References Cited

U.S. PATENT DOCUMENTS 5,238,832 A    8/1993   Johnson et al.

OTHER PUBLICATIONS

Propargyl Alcohol, NCI Technical Resources Inc. Aug. 1996; p. 1-21.*
Barlan et al., "The regio- and stereochemical course of reductive cross-coupling reactions between 1,3-disubstituted allenes and vinylsilanes: Synthesis of (Z)-dienes," Tetrahedron, vol. 66, No. 26, Jun. 26, 2010, pp. 4775-4783.
Deng et al., "Reactions of 2,3-Allenols and Their Derivatives," Chinese Journal of Organic Chemistry, vol. 26, No. 11, 2006, pp. 1468-1484.
Horváth et al., "Mild and efficient palladium(II)-catalyzed racemization of allenes," Chemical Communications, vol. 8, 2004, pp. 964-965, available online on Mar. 9, 2004.
International Search Report and Written Opinion of the International Searching Authority, dated Mar. 14, 2013, issued in International Application No. PCT/CN2012/084896.
Kuang et al., "Copper (I) Iodide-Catalyzed One-Step Preparation of Functionalized Allenes from Terminal Alkynes: Amine Effect," Advanced Synthesis & Catalysis, vol. 354, 2012, available online Mar. 7, 2012, pp. 933-944.

(Continued)

*Primary Examiner* — Samantha Shterengarts
*Assistant Examiner* — Matt Mauro
(74) *Attorney, Agent, or Firm* — Birch, Stewart, Kolasch & Birch, LLP

(57) ABSTRACT

The present invention relates to an optically active axially chiral α-allenic alcohol, a synthesis method and use thereof. The invention relates to a method of preparing a highly optically active chiral α-allenic alcohol by using propargyl alcohol, aldehyde and chiral α,α-diphenyl-L-prolinol under the protection of tert-butyldimethylsilyl with an accelerant zinc bromide. The axially chiral α-allenic alcohol has the structural formula (I). The method of the present invention has the following advantages: the synthesis route is short, operations are simple, raw materials are readily available, separation and purification are convenient, the substrate has high universality, the total yield is high, and enantioselectivity and diastereoselectivity are high. The highly optically active axially chiral α-allenic alcohol synthesized by the method of the present invention can conveniently synthesize 2,5-dihydrofuran compounds having central chirality and complete chirality, and at the same time can further synthesize axially chiral allenic amine and allenic malonic ester compounds having complete chirality.

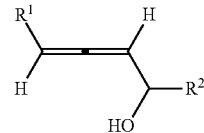

(I)

6 Claims, No Drawings

(56) References Cited

OTHER PUBLICATIONS

Miura et al., "Stereoselective Synthesis of Vinyl-Substituted (Z)-Stilbenes by Rhodium-Catalysed Addition of Arylboronic Acids to Allenic Alcohols," Organic & Biomolecular Chemistry, vol. 8, No. 18, 2010, pp. 4074-4076.
Mundal et al., "A Direct Synthesis of Allenes by a Traceless Petasis Reaction," Journal of the American Chemical Society, vol. 134, No. 13, Mar. 27, 2012, pp. 5782-5785.
Nakamura et al., "Synthesis of mono- and 1,3-disubstituted allenes from propargylic amines via palladium-catalysed hydride-transfer reaction," Organic Biomolecular Chemistry, vol. 6, 2008, available online Mar. 6th, 2008, pp. 1471-1477.
Ye et al., "Catalytic Asymmetric Synthesis of Optically Active Allenes from Terminal Alkynes," Organic Letters, vol. 14, No. 5, Feb. 22, 2012, pp. 1346-1349.

\* cited by examiner

OPTICALLY ACTIVE AXIALLY CHIRAL ALPHA-ALLENIC ALCOHOL, SYNTHESIS METHOD AND USE THEREOF

TECHNICAL FIELD

The present invention relates to a highly optically active axially chiral α-allenic alcohol, a simple and effective synthetic method and the use thereof, specifically to a method of preparing highly optically active axially chiral α-allenic alcohol by using a propargyl alcohol protected by tert-butyldimethylsilyl group, an aldehyde and a chiral α, α-diphenylprolinol as reagents and by using zinc bromide as a mediator.

BACKGROUND OF THE INVENTION

α-allenic alcohol is a very important intermediate in organic syntheses, and is widely used in the syntheses of organic compounds such as 2, 5-dihydrofuran (R. Gelin, S. Gelin, M. Albrand, *Bull. Soc. Chim. Fr.* 1972, 1946; L.-I. Olsson, A. Claesson, *Synthesis* 1979, 743; S. S. Nikam, K.-H. Chu, K. K. Wang, *J. Org. Chem.* 1986, 51, 745; J. A. Mashall, X.-J. Wang, *J. Org. Chem.* 1990, 55, 2995; J. A. Mashall, X.-J. Wang, *J. Org. Chem.* 1991, 56, 4913; J. A. Mashall, K. G. Pinney, *J. Org. Chem.* 1993, 58, 7180; J. A. Mashall, R. H. Yu, J. F. Perkins, *J. Org. Chem.* 1995, 60, 5550; J. A. Mashall, C. A. Sehon, *J. Org. Chem.* 1995, 60, 5966), 2(5H)-furanone (E. Yoneda, T. Kaneko, S.-W. Zhang, K. Onitsuka, S. Takahashi, *Org. Lett.* 2000, 2, 441; X. Cheng, X. Jiang, Y. Yu, S. Ma, *J. Org. Chem.* 2008, 73, 8960), ethyl-oxacyclopropane (R. W. Friesen, M. Blouin, *J. Org. Chem.* 1993, 58, 1653; S.-K. Kang, T. Yamaguchi, S.-J. Pyun, Y.-T. Lee, T.-G. Bail, *Tetrahedron Lett.* 1998, 39, 2127; S. Ma, S. Zhao, *J. Am. Chem. Soc.* 1999, 121, 7943), β-halo-β,γ-olefine aldehydes or β-halo-β,γ-olefine ketones (J. Li, C. Fu, G. Chen, G. Chai, S. Ma, *Adv. Synth. Catal.* 2008, 350, 1376; C. Fu, J. Li, S. Ma, *Chem. Commun.* 2005, 4119; J.-Q. He, D. Shibata, C. Ohno, S. Okamoto, *Tetrahedron Lett.* 2008, 49, 6724), 1, 3-conjugated dienes (S. Ma, G. Wang, *Tetrahedron Lett.* 2002, 43, 5723; Y. Deng, X. Jin, S. Ma, *J. Org. Chem.* 2007, 72, 5901) and allyl alcohols (Z. Lu, S. Ma, *Adv. Synth. Catal.* 2007, 349, 1225). Also, α-allenic alcohol is an important precuror for synthesizing a series of functionalized allenic compounds such as allenic amines (C. Sahlberg, S. B. Ross, I. Fagervall, A.-L. Ask, A. Claesson, *J. Med. Chem.* 1983, 26, 103; Y. Imada, M. Nishida, K. Kutsuwa, S.-I. Murahashi, T. Naota, *Org. Lett.* 2005, 7, 5837; B. M. Trost, D. R. Fandrick, D. C. Dinh, *J. Am. Chem. Soc.* 2005, 127, 14186), allenic malonate (M. Ogasawara, H. Ikeda, T. Nagano, T. Hayashi, *J. Am. Chem. Soc.* 2001, 123, 2089; Y. Imada, K. Ueno, K. Kutsuwa, S.-I. Murahashi, *Chem. Lett.* 2002, 140; S. Ma, N. Jiao, S. Zhao, H. Hou, *J. Org. Chem.,* 2002, 67, 2837) allenyl mercaptan (N. Morita, N. Krause, *Angew. Chem., Int. Ed.* 2006, 45, 1897) and allenyl aldehydes or ketones (S. Ma, S. Yu, S. Yin, *J. Org. Chem.* 2003, 68, 8996; b) S. Ma, J. Liu, S. Li, B. Chen, J. Cheng, J. Kuang, Y. Liu, B. Wan, Y. Wang, J. Ye, Q. Yu, W. Yuan, S. Yu, *Adv. Synth. Catal.* 2011, 353, 1005). Among a series of α-allenic alcohols, axially chiral α-allenic alcohols are particularly important, because the axial chirality can be converted to central chirality by the chirality transferring strategy, which provides an effective route for synthesizing optically active compounds. Therefore, it is very significant to develop a method for conveniently and effectively synthesizing highly optically active axially chiral α-allenic alcohols. It's been reported that the syntheses of axially chiral α-allenic alcohols usually required complicated multiple steps and strict reaction conditions, and the total yields were very low. Moreover, most of those methods use dangerous chemicals such as n-butyllithium (n-BuLi), or ethylmagnesium bromide (EtMgBr) and lithium aluminum hydroxide (LiAlH$_4$), which results in an inconvenient operation and is unsuitable for the syntheses in large scale (L.-I. Olsson, A. Claesson, *Acta Chem. Scand.* 1977, B31, 614; A. Claesson, L.-I. Olsson, *J. Am. Chem. Soc.* 1979, 101, 7302; R. A. Smith, R. L. White, A. Krantz, *J. Med. Chem.* 1988, 31, 1558; J. Stichler-Bonaparte, H. Kruth, R. Lunkwitz, C. Tschierske, *Liebigs Ann.* 1996, 1375).

The present invention overcomes the defects of the prior arts such as long synthetic route, low yield, the use of dangerous chemicals and inconvenient operations etc., and provides a method for conveniently and effectively preparing a highly optically active axially chiral α-allenic alcohol by using a propargyl alcohol protected by tert-butyldimethylsilyl group, an aldehyde and a chrial α, α-diphenylprolinol as reagents and by using zinc bromide as a mediator. As compared with the conventional methods, the present method has the advantages of short synthetic route, high yield, convenient operation, and good suitability for the synthesis in large scale.

SUMMARY OF THE INVENTION

An object of the present invention is to provide a highly optically active axially chiral α-allenic alcohol, a simple and effective synthetic method and the use thereof.

The present invention provides an axially chiral α-allenic alcohol having the following structural formula:

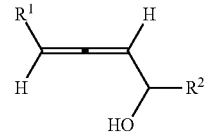

wherein $R^1$ is a $C_1$-$C_{10}$ hydrocarbon group, such as a linear alkyl, cycloalkyl, or phenyl group, etc.; $R^2$ is H or a $C_1$-$C_{10}$ hydrocarbon group such as linear alkyl, cycloalkyl, or phenyl group, etc.; the axial chirality of the allene is in R or S configuration; the carbon atom linked to the hydroxyl may be non-chiral, or in R or S configuration; and when the $C_1$-$C_{10}$ hydrocarbon group is an aliphatic group, the ee value is higher than 96%.

The present invention further provides a method for synthesizing an axially chiral α-allenic alcohol, which has a following reaction equation:

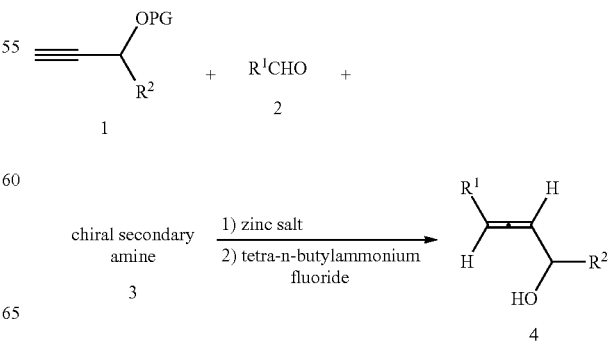

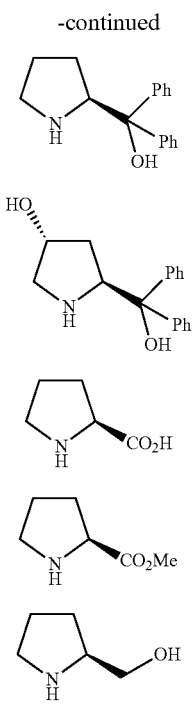

wherein PG represents a silyl protective group, and R¹, R², the axial chirality of the allene, and the configuration of the carbon atom linked to the hydrodroxyl are the same as aforementioned.

The axially chiral α-allenic alcohol can be obtained by using (S)-3 or its enantiomers as a chiral secondary amine with a propargyl alcohol protected by silyl group and an aldehyde by using zinc bromide as a mediator for 5-15 hours in an organic solvent at a temperature of 100-130° C., followed by passing through a short silica-gel chromatographic column and then removing the silyl protective group with tetra-n-butylammonium fluoride; wherein the molar ratio of the propargyl alcohol protected by silyl protective group: aldehyde:chiral secondary amine:zinc salt:tetra-n-butylammonium fluoride is 1-3:1-3:1:0.5-1.5:1-5; said silyl group is trimethylsilyl, triisopropylsilyl, tert-buytldimethysilyl, or tert-butyldiphenylsilyl group, preferably tert-buytldimethysilyl group; said chiral secondary amine is (S)-3a-e or its enantiomers, preferably (S)-3a or its enantiomers; said zinc salt is zinc chloride, zinc bromide, zinc iodide, zinc acetate, or zinc trifluoromethanesulfonate, preferably zinc bromide; said tetra-n-butylammonium fluoride is tetra-n-butylammonium fluoride trihydrate or a tetrahydrofuran solution of tetra-n-butylammonium fluoride; said organic solvent is benzene, toluene, chlorobenzene, p-xylene, o-xylene, m-xylene, or sym-trimethylbenzene, preferably toluene.

A more specific method can be as follows:

Adding a zinc salt, a chiral secondary amine, a propargyl alcohol with a protective silyl group, an aldehyde, and a dehydrated organic solvent into a dried reactor, and stirring for 5-20 hours at 100-130° C. After the reaction, the reaction product is passed through a short silica-gel chromatographic column so as to obtain a crude product after evaporation. The crude product is then dissolved in the organic solvent, added with tetra-n-butylammonium fluoride at 0° C., and then stirred for 1-15 hours at room temperature. After the reaction, the mixture is washed with water, extracted with an organic solvent, and then dried with anhydrous sodium sulfate, evaporated, and purified by column chromatographic separation, so as to obtain an axially chiral α-allenic alcohol.

The present invention relates to a method for effectively preparing axially chiral α-allenic alcohol, by using zinc dibromide as a mediator and by using a propargyl alcohol protected by tert-butyldimethylsilyl group, an aldehyde and a chiral α, α-diphenylprolinol as reagents, via two steps operation, so as to obtain a highly optically active axially chiral α-allenic alcohol. With this method, axially chiral α-allenic primary or secondary alcohols having different substituent groups can be synthesized. By using a S configured α, α-diphenylprolinol, an allenic product having the R configured axial chirality can be obtained; whereas by using a R configured α, α-diphenylprolinol, an allenic product having the S configured axial chirality can be obtained. When an optically active propargyl alcohol protected by tert-butyldimethylsilyl is used as a raw material, by using different configured raw materials and an α, α-diphenylprolinol, all four isomers of axially chiral α-allenic secondary alcohols having both axial and central chirality can be synthesized conveniently.

When using the highly optically active axially chiral α-allenci alcohol synthesized according to the method of the present invention, 2, 5-dihydrofuran compounds having central chirality can be conveniently synthesized with highly efficient chirality transfer, and the axially chiral allenic amines and allenic malonate compounds can also be synthesized without racemization.

The method of the present invention has the advantages of short synthetic route, simple operation, readily available raw materials, convenient separation and purification, broad-spectrum of substrate, high yield, and high enantioselectivity and diastereoselectivity, which overcomes the defects of the prior arts such as long synthesis route, low productivity, stringent reaction conditions, use of dangerous chemicals and inconvenient operations, etc.

PREFERRED EMBODIMENTS OF THE INVENTION

The following examples are given for the further understanding of the present invention and are not intended to limit the present invention.

Example 1

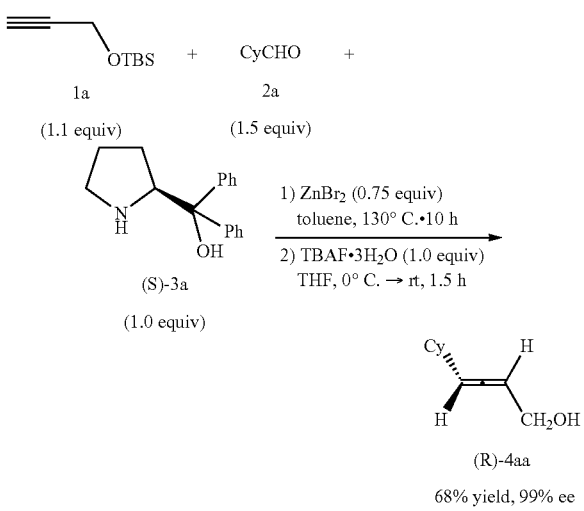

wherein "equiv" represents equivalent, "mol" represents mole, "TBS" represents tert-butyldimethylsilyl, "Cy" represents cyclohexyl, "TBAF" represents tetrabutylammonium fluoride, "THF" represents tetrahydrofuran, "rt" refers to room temperature, "ee" represents enantiomeric excess, and "de" represents diastereomeric excess.

Under the protection of an inert gas, ZnBr$_2$ (169.3 mg, 0.75 mmol) was added to a dried reaction tube, dried with heating gun. Then α, α-diphenylprolinol (S)-3a (258.7 mg, 1.0 mmol, 98%), propargyl alcohol protected by tert-butyldimethylsilyl group 1a (188.2 mg, 1.1 mmol), dehydrated toluene (2 mL), newly distilled cyclohexanecarboxaldehyde 2a (168.6 mg, 1.5 mmol), and dehydrated toluene (1 mL) were added. The reaction tube was then equipped with a reflux condensing tube, and placed into an oil bath that had been previously heated to 130° C. and stirred under reflux for 10 hours. After cooled to the room temperature, the product was filtered with a short silica-gel chromatographic column, washed with 20 mL of ether, evaporated and passed through a short column (petroleum ether/ether=50/1), and then the crude reaction product of allenic alcohol protected by tert-butyldimenthylsilyl group was obtained. The crude product was directly dissolved in tetrahydrofuran (3 mL), to which was added with TBAF.3H$_2$O (316.0 mg, 1.0 mmol) at 0° C. After the temperature was naturally increased to room temperature, the resulting mixture was stirred for 1.5 hours, and added to a mixture of 10 mL of ether and 10 mL of water; the organic layer was separated and the water layer was extracted with ether (10 mL×3). The organic layers were combined, dried with anhydrous sodium sulfate, evaporated, and subjected to the column chromatography (petroleum ether/ethyl acetate=10/1) to afford a liquid: axially chiral α-allenic alcohol(R)-4aa (104.0 mg, 68%): 99% ee (HPLC measurement conditions: Chiralcel AS-H column, n-hexane/isopropanol=98/2, 0.6 mL/min, λ=214 nm, $t_R$(large peak)=16.0 min, $t_R$(small peak)=19.2 min); $[α]22_D$=-99.8 (c=1.01, CHCl$_3$); $^1$H NMR (300 MHz, CDCl$_3$) δ=5.41-5.24 (m, 2H, CH=C=CH), 4.10 (d, J=2.7 Hz, 2H, OCH$_2$), 2.08-1.88 (m, 2H, OH and CH from Cy), 1.82-1.57 (m, 5H, protons from Cy), 1.37-0.97 (m, 5H, protons from Cy); $^{13}$C NMR (75 MHz, CDCl$_3$) δ=201.9, 99.7, 92.5, 60.8, 37.0, 33.0, 32.9, 26.0, 25.9; MS (EI) m/z (%): 152 (M$^+$, 0.70), 55 (100); IR (neat): ν=3326, 2923, 2850, 1961, 1448, 1302, 1259, 1214, 1062, 1008 cm$^{-1}$; HRMS [M$^+$] calculated value: 152.1201, measured value: 152.1203.

Example 2

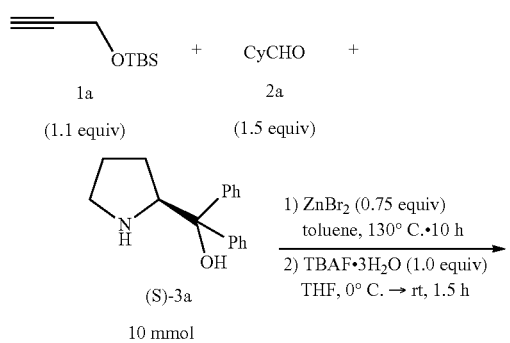

(R)-4aa

70% yield, 99% ee

Operations were conducted by referring to Example 1: Using ZnBr$_2$ (1.6912 g, 7.5 mmol), α, α-diphenylprolinol (S)-3a (2.5857 g, 10 mmol), propargyl alcohol protected by tert-butyldimethylsilyl group 1a (1.8738 g, 11 mmol), newly distilled cyclohexanecarboxaldehyde 2a (1.6831 g, 15 mmol), dehydrated toluene (30 mL), TBAF.3H$_2$O (3.1563 g, 10 mmol) and tetrahydrofuran (30 mL), column chromatography (pertroleum ether/ethyl acetate=15/1 (800 mL)→10:1) to afford a liquid: axially chiral α-allenic alcohol (R)-4aa (1.0624, 70%): 99% ee (HPLC measurement conditions: Chiralcel AS-H column, n-hexane/isopropanol=98/2, 0.6 mL/min, λ=214 nm, $t_R$(large peak)=11.9 min, $t_R$(small peak)=12.9 min); $[α]^{22}_D$=-100.3 (c=1.00, CHCl$_3$); $^1$H NMR (300 MHz, CDCl$_3$) δ=5.42-5.26 (m, 2H, CH=C=CH), 4.11 (s, 2H, OCH$_2$), 2.07-1.94 (m, 1H, CH from Cy), 1.82-1.49 (m, 6H, OH and protons from Cy), 1.36-1.00 (m, 5H, protons from Cy).

Example 3

(R)-4ab

45% yield, 98% ee

Operations were conducted by referring to Example 1: Using ZnBr$_2$ (506.8 mg, 2.25 mmol), α, α-diphenylprolinol (S)-3a (775.4 mg, 3.0 mmol), propargyl alcohol protected by tert-butyldimethylsilyl group 1a (562.4 mg, 3.3 mmol), newly distilled iso-pentaldehyde 2b (388.1 mg, 4.5 mmol), dehydrated toluene (9 mL), TBAF.3H$_2$O (947.3 mg, 3.0 mmol) and tetrahydrofuran (5 mL), column chromatography (petroleum ether/ethyl acetate=15/1) to afford a liquid: axially chiral α-allenic alcohol(R)-4ab (171.2 mg, 45%): 98% ee (HPLC measurement conditions: Chiralcel AD-H column, n-hexane/isopropanol=200/1, 1.0 mL/min, λ=214 nm, $t_R$(large peak)=20.4 min, $t_R$(small peak)=25.3 min); $[α]^{22}_D$=-80.3 (c=1.01, CHCl$_3$); $^1$H NMR (300 MHz, CDCl$_3$) δ=5.35-5.18 (m, 2H, CH=C=CH), 4.11 (s, 2H, OCH$_2$), 2.03-1.79 (m, 3H, OH and CH$_2$), 1.76-1.58 (m, 1H, CH), 0.92 (d, J=6.6 Hz, 6H, two CH₃); $^{13}$C NMR (75 MHz, CDCl₃) δ=203.6, 92.2, 90.9, 60.8, 38.1, 28.3, 22.1; MS (EI) m/z (%): 126 (M⁺, 0.21), 55 (100); IR (neat): v=3326, 2955, 2928, 2870, 1963, 1466, 1384, 1367, 1262, 1056, 1013 cm$^{-1}$; HRMS [M⁺] calculated value: 126.1045, measured value: 126.1044.

Example 4

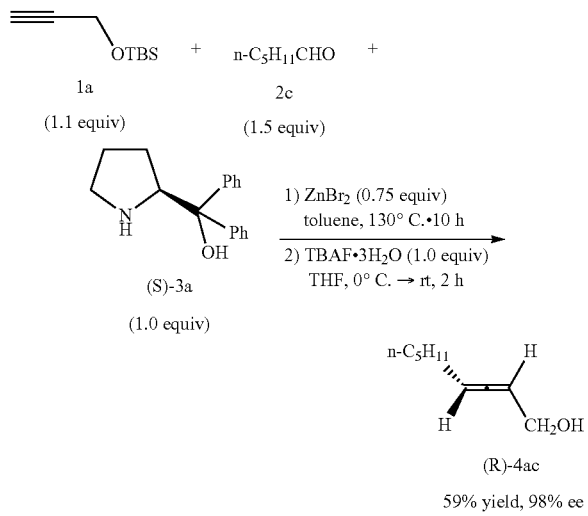

Operations were conducted by referring to Example 1: Using ZnBr₂ (169.7 mg, 0.75 mmol), α, α-diphenylprolinol (S)-3a (258.8 mg, 1.0 mmol), propargyl alcohol protected by tert-butyldimethylsilyl group 1a (188.2 mg, 1.1 mmol), newly distilled n-hexanal 2c (150.4 mg, 1.5 mmol), dehydrated toluene (3 mL), TBAF·3H₂O (316.2 mg, 1.0 mmol) and tetrahydrofuran (3 mL), column chromatography (petroleum ether/ethyl acetate=10/1) to afford a liquid: axially chiral a-allenic alcohol (R)-4ac (83.0 mg, 59%): 98% ee (HPLC measurement conditions: Chiralcel AS-H column, n-hexane/isopropanol=98/2, 0.5 mL/min, λ=214 nm, $t_R$(large peak)=12.2 min, $t_R$(small peak)=13.1 min); $[α]^{21}_D$=−78.4 (c=1.03, CHCl₃); $^1$H NMR (300 MHz, CDCl₃) δ=5.36-5.23 (m, 2H, CH=C=CH), 4.11 (s, 2H, OCH₂), 2.09-1.90 (m, 3H, OH and CH₂), 1.49-1.23 (m, 6H, three CH₂), 0.89 (t, J=6.5 Hz, 3H, CH₃); $^{13}$C NMR (75 MHz, CDCl₃) δ=203.0, 93.7, 91.6, 60.7, 31.2, 28.7, 28.5, 22.4, 14.0; MS (EI) m/z (%): 140 (M⁺, 0.15), 55 (100); IR (neat): v=3345, 2956, 2928, 2857, 1963, 1464, 1417, 1379, 1206, 1137, 1111, 1057, 1011 cm$^{-1}$; HRMS [M⁺] calculated value: 140.1201, measured value: 140.1202.

Example 5

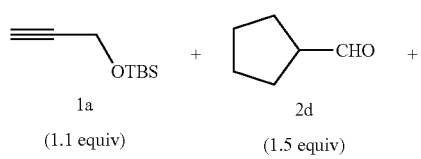

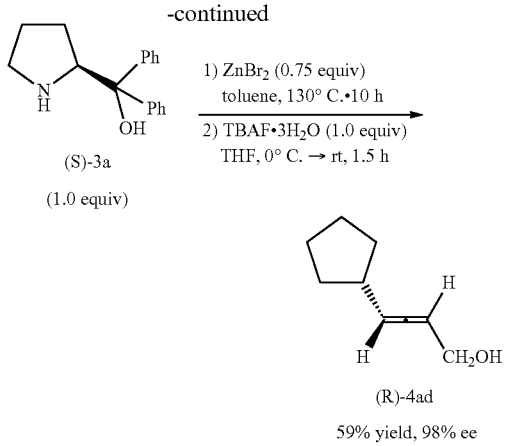

Operations were conducted by referring to Example 1: Using ZnBr₂ (169.4 mg, 0.75 mmol), α, α-diphenylprolinol (S)-3a (258.2 mg, 1.0 mmol), propargyl alcohol protected by tert-butyldimethylsilyl group 1a (188.2 mg, 1.1 mmol), newly distilled cyclohexanecarboxaldehyde 2d (147.3 mg, 1.5 mmol), dehydrated toluene (3 mL), TBAF·3H₂O (316.4 mg, 1.0 mmol) and tetrahydrofuran (3 mL), column chromatography (petroleum ether/ethyle acetate=10/1) to afford a liquid: axially chiral α-allenic alcohol (R)-4ad (81.9 mg, 59%): 98% ee (HPLC measurement conditions: Chiralcel AS-H column, n-hexane/isopropanol=98/2, 0.6 mL/min, λ=214 nm, $t_R$(large peak)=13.8 min, $t_R$(small peak)=15.3 min); $[α]^{20}_D$=−97.2 (c=1.02, CHCl₃); $^1$H NMR (300 MHz, CDCl₃) δ=5.39-5.27 (m, 2H, CH=C=CH), 4.10 (d, J=2.7 Hz, 2H, OCH₂), 2.56-2.39 (m, 1H, CH from cyclopentyl), 2.07 (s, 1H, OH), 1.86-1.72 (m, 2H, CH₂), 1.72-1.47 (m, 4H, two CH₂), 1.46-1.28 (m, 2H, CH₂); $^{13}$C NMR (75 MHz, CDCl₃) δ=201.8, 98.6, 92.4, 60.7, 39.0, 32.7, 24.8; MS (EI) m/z (%): 138 (M⁺, 0.28), 79 (100); IR (neat): v=3321, 2951, 2867, 1961, 1451, 1420, 1207, 1009 cm$^{-1}$; HRMS [M⁺] calculated value: 138.1045, measured value: 138.1044.

Example 6

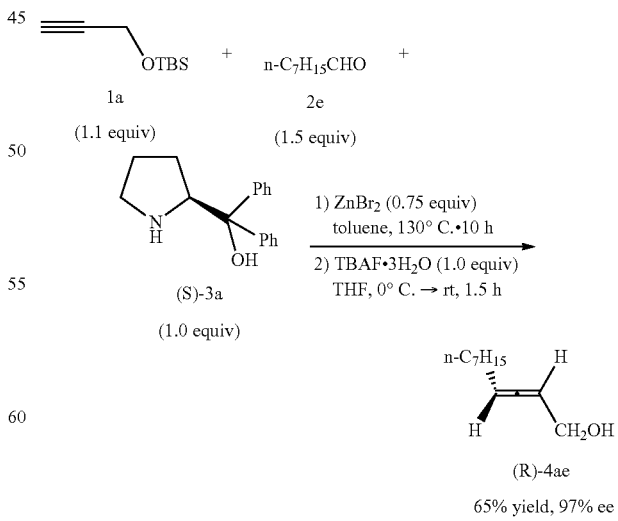

Operations were conducted by referring to Example 1: Using ZnBr₂ (169.5 mg, 0.75 mmol), α, α-diphenylprolinol (S)-3a (258.3 mg, 1.0 mmol), propargyl alcohol protected by tert-butyldimethylsilyl group 1a (188.2 mg, 1.1 mmol), newly distilled n-octanal 2e (192.5 mg, 1.5 mmol), dehydrated toluene (3 mL), TBAF·3H$_2$O (315.7 mg, 1.0 mmol) and tetrahydrofuran (3 mL), column chromatography (petroleum ether/ethyl acetate=15/1) to afford a liquid: axially chiral a-allenic alcohol (R)-4ae (109.8 mg, 65%): 97% ee (HPLC measurement conditions: Chiralcel AS-H column, n-hexane/isopropanol=98/2, 0.6 mL/min, λ=214 nm, $t_R$(large peak)=11.1 min, $t_R$(small peak)=12.2 min); $[α]^{20}_D$=−66.1 (c=1.03, CHCl$_3$); $^1$H NMR (300 MHz, CDCl$_3$) δ=5.37-5.22 (m, 2H, CH=C=CH), 4.11 (d, J=1.2 Hz, 2H, OCH$_2$), 2.07-1.95 (m, 2H, CH$_2$), 1.91 (s, 1H, OH), 1.47-1.17 (m, 10H, five CH$_2$), 0.88 (t, J=6.5 Hz, 3H, CH$_2$); $^{13}$C NMR (75 MHz, CDCl$_3$) δ=202.9, 93.8, 91.6, 60.7, 31.8, 29.08, 29.06, 29.0, 28.6, 22.6, 14.0; MS (ESI): m/z 191 (M+Na$^+$), 168 (M$^+$); IR (neat): ν=3320, 2956, 2925, 2855, 1964, 1463, 1420, 1379, 1140, 1056, 1012 cm$^{-1}$; HRMS [M$^+$] calculated value: 168.1514, measured value: 168.1515.

Example 7

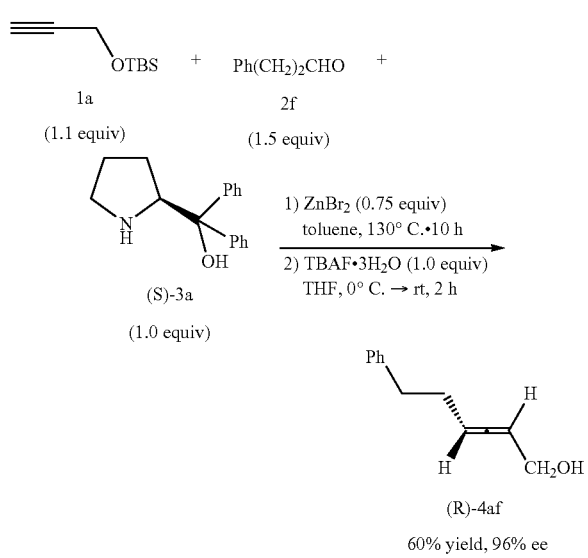

(R)-4af

60% yield, 96% ee

Operations were conducted by referring to Example 1: Using ZnBr$_2$ (169.7 mg, 0.75 mmol), α, α-diphenylprolinol (S)-3a (258.6 mg, 1.0 mmol), propargyl alcohol protected by tert-butyldimethylsilyl group 1a (187.9 mg, 1.1 mmol), newly distilled phenylpropyl aldehyde 2f (202.1 mg, 1.5 mmol), dehydrated toluene (3 mL), TBAF·3H$_2$O (315.7 mg, 1.0 mmol) and tetrahydrofuran (3 mL), column chromatography (petroleum ether/ethyl acetate=15/1 (320 mL)→10:1) to afford a liquid: axially chiral α-allenic alcohol (R)-4af (105.1 mg, 60%): 96% ee (HPLC measurement conditions: Chiralcel AS-H column, n-hexane/isopropanol=100/1, 1.0 mL/min, λ=214 nm, $t_R$(large peak)=19.0 min, $t_R$(small peak)=20.5 min); $[α]^{20}_D$=−38.7 (c=1.05, CHCl$_3$); $^1$H NMR (300 MHz, CDCl$_3$) δ=7.32-7.13 (m, 5H, Ar—H), 5.34-5.21 (m, 2H, CH=C=CH), 3.97 (d, J=1.2 Hz, 2H, OCH$_2$), 2.83-2.64 (m, 2H, CH$_2$), 2.45-2.24 (m, 2H, CH$_2$), 1.78 (s, 1H, OH); $^{13}$C NMR (75 MHz, CDCl$_3$) δ=203.2, 141.3, 128.4, 128.2, 125.8, 92.7, 92.1, 60.4, 35.0, 29.9; MS (EI) m/z (%): 174 (M$^+$, 0.12), 91 (100); IR (neat): ν=3341, 3026, 2923, 2856, 1963, 1495, 1453, 1062, 1008 cm$^{-1}$; HRMS [M$^+$] calculated value: 174.1045, measured value: 174.1044.

Example 8

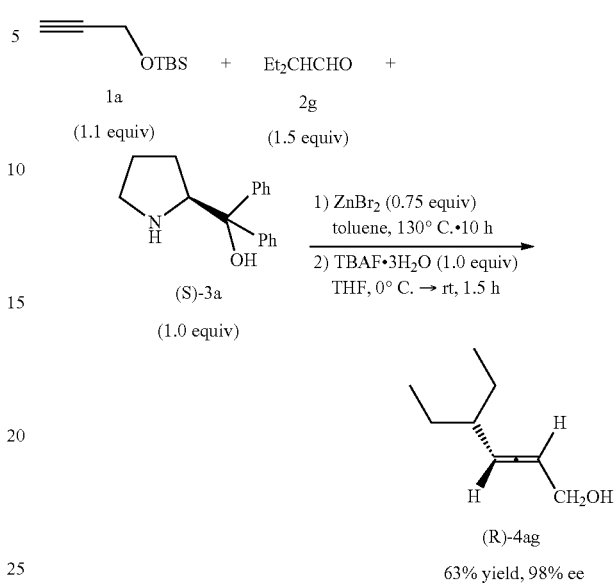

(R)-4ag

63% yield, 98% ee

Operations were conducted by referring to Example 1: Using ZnBr$_2$ (169.2 mg, 0.75 mmol), α, α-diphenylprolinol (S)-3a (258.7 mg, 1.0 mmol), propargyl alcohol protected by tert-butyldimethylsilyl group 1a (188.1 mg, 1.1 mmol), newly distilled 2-ethyl butanal 2g (150.4 mg, 1.5 mmol), dehydrated toluene (3 mL), TBAF·3H$_2$O (315.8 mg, 1.0 mmol) and tetrahydrofuran (3 mL), column chromatography (petroleum ether/ethyl acetate=15/1) to afford a liquid: axially chiral α-allenic alcohol (R)-4ag (88.7 mg, 63%): 98% ee (HPLC measurement conditions: Chiralcel AD-H column, n-hexane/isopropanol=200/1, 1.0 mL/min, λ=214 nm, $t_R$(large peak)=19.0 min, $t_R$(small peak)=22.0 min); $[α]^{20}_D$=−92.5 (c=1.01, CHCl$_3$); $^1$H NMR (300 MHz, CDCl$_3$) δ=5.32 (q, J=6.1 Hz, 1H, one proton from CH=C=CH), 5.14-5.04 (m, 1H, one proton from CH=C=CH), 4.11 (d, J=3.6 Hz, 2H, OCH$_2$), 2.05 (s, 1H, OH), 1.95-1.80 (m, 1H, CH), 1.53-1.20 (m, 4H, two CH$_2$), 0.90 (t, J=7.4 Hz, 6H, two CH$_3$); $^{13}$C NMR (75 MHz, CDCl$_3$) δ=202.9, 97.3, 91.5, 61.0, 42.7, 27.5, 27.3, 11.54, 11.46; MS (EI) m/z (%): 140 (M$^+$, 0.15), 93 (100); IR (neat): ν=3323, 2988, 2871, 1963, 1459, 1381, 1359, 1141, 1011 cm$^{-1}$; HRMS [M$^+$] calculated value: 140.1201, measured value: 140.1199.

Example 9

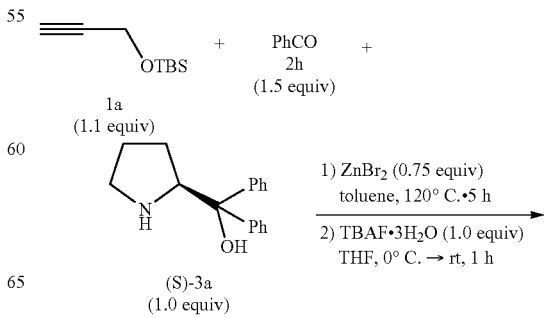

-continued

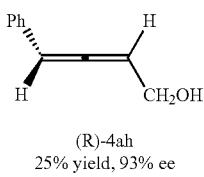

(R)-4ah
25% yield, 93% ee

Operations were conducted by referring to Example 1: The reaction temperature in the first step was 120° C.; using ZnBr$_2$ (169.7 mg, 0.75 mmol), α, α-diphenylprolinol (S)-3a (258.3 mg, 1.0 mmol), propargyl alcohol protected by tert-butyldimethylsilyl group 1a (188.0 mg, 1.1 mmol), newly distilled benzaldehyde 2h (159.5 mg, 1.5 mmol), dehydrated toluene (3 mL), TBAF·3H$_2$O (315.7 mg, 3.0 mmol) and tetrahydrofuran (3 mL), column chromatography (petroleum ether/ethyl acetate=8/1) to afford a liquid: axially chiral α-allenic alcohol (R)-4ah (37.0 mg, 25%): 93% ee (HPLC measurement conditions: Chiralcel AD-H column, n-hexane/isopropanol=98/2, 1.0 mL/min, λ=214 nm, $t_R$(small peak)=20.1 min, $t_R$(large peak)=21.5 min; $[\alpha]^{20}_D$=−217.1 (c=0.45, CHCl$_3$); $^1$H NMR (300 MHz, CDCl$_3$) δ=7.35-7.14 (m, 5H, Ar—H), 6.35-6.27 (m, 1H, CH═C═CH), 4.11 (q, J=5.8 Hz, 1H, OCH), 4.24 (t, J=2.4 Hz, 1H, OCH), 1.84 (s, 1H, OH); $^{13}$C NMR (75 MHz, CDCl$_3$) δ=204.2, 133.7, 128.6, 127.2, 126.8, 97.1, 95.8, 60.3; MS (EI) m/z (%): 146 (M$^+$, 23.71), 55 (100); IR (neat): ν=3327, 3031, 2928, 2871, 1950, 1598, 1494, 1459, 1408, 1264, 1205, 1112, 1072, 1009 cm$^{-1}$; HRMS [M$^+$] calculated value: 146.0732, measured value: 146.0731.

Example 10

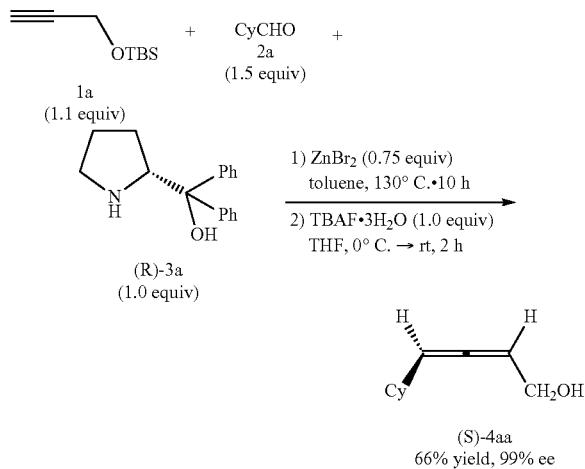

Operations were conducted by referring to Example 1: Using ZnBr$_2$ (169.4 mg, 0.75 mmol), α, α-diphenylprolinol (R)-3a (258.3 mg, 1.0 mmol), propargyl alcohol protected by tert-butyldimethylsilyl group 1a (188.3 mg, 1.1 mmol), newly distilled cyclohexanecarboxaldehyde 2a (169.0 mg, 1.5 mmol), dehydrated toluene (3 mL), TBAF·3H$_2$O (315.8 mg, 1.0 mmol) and tetrahydrofuran (3 mL), column chromatography (petroleum ether/ethyl acetate=10/1) to afford a liquid: axially chiral α-allenic alcohol (S)-4aa (99.9 mg, 66%): 99% ee (HPLC measurement conditions: Chiralcel AS-H column, n-hexane/isopropanol=98/2, 0.6 mL/min, λ=214 nm, $t_R$(small peak)=16.0 min, $t_R$(large peak)=19.0 min); $[\alpha]^{21}_D$=100.9 (c=1.04, CHCl$_3$); $^1$H NMR (300 MHz, CDCl$_3$) δ=5.41-5.26 (m, 2H, CH═C═CH), 4.11 (s, 2H, OCH$_2$), 2.08-1.94 (m, 1H, CH from Cy), 1.82-1.57 (m, 6H, OH and protons from Cy), 1.37-1.00 (m, 5H, protons from Cy); $^{13}$C NMR (75 MHz, CDCl$_3$) δ=201.8, 99.9, 92.6, 60.8, 37.0, 33.03, 32.97, 26.0, 25.9; MS (EI) m/z (%): 152 (M$^+$, 1.15), 55 (100); IR (neat): ν=3321, 2923, 2850, 1961, 1448, 1417, 1348, 1062, 1009 cm$^{-1}$; HRMS [M$^+$] calculated value: 152.1201, measured value: 152.1202.

Example 11

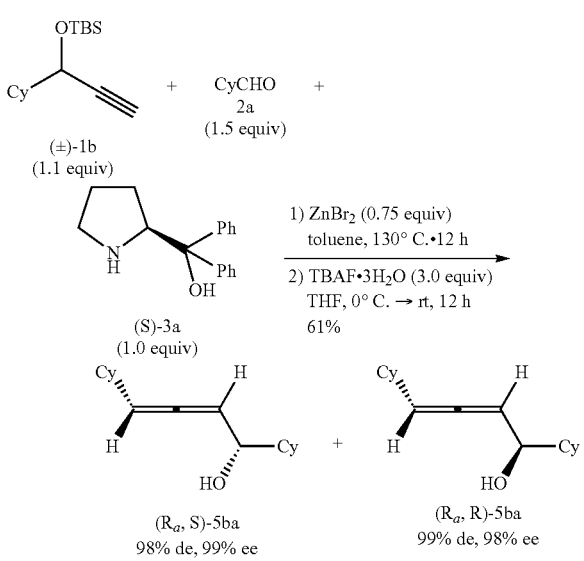

The value 61% under arrow shown in the reaction equation represents the yield, and the value de represents diastereomeric excess. The same symbols in the following Examples herein represent the same meanings.

Operations were conducted by referring to Example 1: Using ZnBr$_2$ (169.3 mg, 0.75 mmol), α, α-diphenylprolinol (S)-3a (258.5 mg, 1.0 mmol), propargyl alcohol protected by tert-butyldimethylsilyl group (±)-1b (277.9 mg, 1.1 mmol), newly distilled cyclohexanecarboxaldehyde 2a (168.2 mg, 1.5 mmol), dehydrated toluene (3 mL), TBAF·3H$_2$O (946.9 mg, 3.0 mmol) and tetrahydrofuran (3 mL), column chromatography (petroleum ether/ethyl acetate=25/1) to afford a liquid: axially chiral α-allenic alcohol 5ba (143.5 mg, 61%): ($R_a$, S)-5ba (98% de, 99% ee), ($R_a$, R)-5ba (99% de, 98% ee) (HPLC measurement conditions: Chiralcel PC-2 column, n-hexane/isopropanol=98/2, 0.5 mL/min, λ=214 nm, $t_R$(small peak)=9.4 min, $t_R$(large peak)=10.3 min, $t_R$(large peak)=11.5 min, $t_R$(small peak)=12.6 min); $[\alpha]^{21}_D$=−81.8 (c=1.01, CHCl$_3$); $^1$H NMR (300 MHz, CDCl$_3$) δ=5.33-5.19 (m, 2H, CH═C═CH), 3.87 (s, 1H, OCH), 2.06-1.57 (m, 12H, OH and protons from Cy), 1.49-0.94 (m, 11H, protons from Cy); $^{13}$C NMR (75 MHz, CDCl$_3$) δ=201.4, 200.9, 100.3, 99.8, 95.1, 94.9, 74.5, 73.9, 44.08, 43.97, 37.12, 37.09, 33.04, 33.01, 32.97, 28.73, 28.70, 28.3, 28.2, 26.5, 26.11, 26.07, 26.05, 26.00, 25.98, 25.91; MS (EI) m/z (%): 234 (M$^+$, 2.25), 55 (100); IR (neat): ν=3376, 2922, 2851, 1960, 1448, 1083, 1009 cm$^{-1}$; HRMS [M$^+$] calculated value: 234.1984, measured value: 234.1980.

Example 12

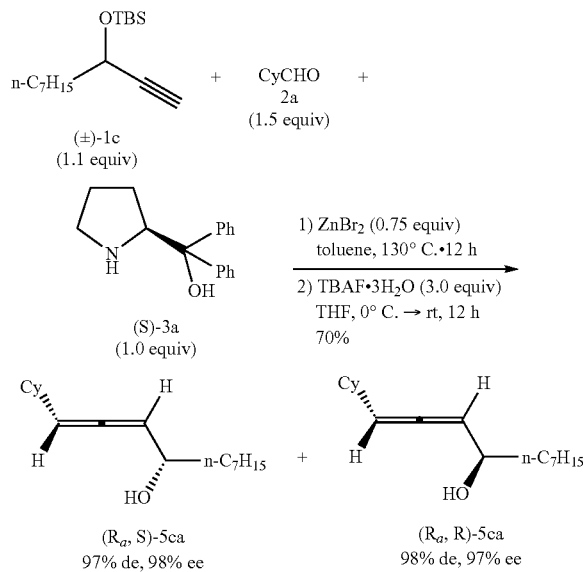

Operations were conducted by referring to Example 1: Using ZnBr₂ (169.3 mg, 0.75 mmol), α,α-diphenylprolinol (S)-3a (258.8 mg, 1.0 mmol), propargyl alcohol protected by tert-butyldimethylsilyl group (±)-1c (295.7 mg, 1.1 mmol), newly distilled cyclohexanecarboxaldehyde 2a (168.5 mg, 1.5 mmol), dehydrated toluene (3 mL), TBAF.3H₂O (947.2 mg, 3.0 mmol) and tetrahydrofuran (3 mL), column chromatography (petroleum ether/ethyl acetate=25/1) to afford a liquid: axially chiral α-allenic alcohol 5ca (175.8 mg, 70%): (R$_a$, S)-5ca (97% de, 98% ee), (R$_a$, R)-5ca (98% de, 97% ee) (HPLC measurement conditions: Chiralcel IC column, n-hexane/isopropanol=100/1, 0.5 mL/min, λ=214 nm, t$_R$(small peak)=14.0 min, t$_R$(large peak)=14.8 min, t$_R$(large peak)=16.8 min, t$_R$(small peak)=17.4 min); $[\alpha]^{21}_D$=−70.2 (c=1.03, CHCl₃); ¹H NMR (300 MHz, CDCl₃) δ=5.32-5.19 (m, 2H, CH=C=CH), 4.10 (s, 1H, OCH), 2.07-1.48 (m, 9H, OH and protons from Cy and n-C₇H₁₅), 1.48-0.99 (m, 15H, protons from Cy and n-C₇H₁₅), 0.88 (t, J=5.7 Hz, 3H, CH₃); ¹³C NMR (75 MHz, CDCl₃) δ=201.1, 200.7, 100.4, 99.8, 96.8, 96.6, 70.3, 69.8, 37.6, 37.5, 37.1, 33.04, 32.99, 31.7, 29.5, 29.4, 29.2, 26.0, 25.9, 25.44, 25.39, 22.6, 14.0; MS (EI) m/z (%): 250 (M⁺, 0.61), 55 (100); IR (neat): v=3346, 2923, 2852, 1961, 1448, 1134, 1047, 1017 cm⁻¹; HRMS [M⁺] calculated value: 250.2297, measured value: 250.2298.

Example 13

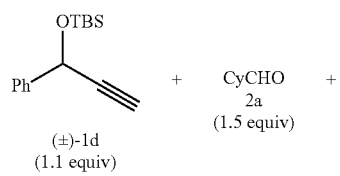

Operations were conducted by referring to Example 1: Using ZnBr₂ (169.4 mg, 0.75 mmol), α,α-diphenylprolinol (S)-3a (258.5 mg, 1.0 mmol), propargyl alcohol protected by tert-butyldimethylsilyl group (±)-1d (271.4 mg, 1.1 mmol), newly distilled cyclohexanecarboxaldehyde 2a (169.1 mg, 1.5 mmol), dehydrated toluene (3 mL), TBAF.3H₂O (947.2 mg, 3.0 mmol) and tetrahydrofuran (3 mL), column chromatography (petroleum ether/ethyl acetate=15/1) to afford a liquid: axially chiral α-allenic alcohol 5da (167.2 mg, 73%): (R$_a$, S)-5da (99% de, 99% ee), (R$_a$, R)-5da (99% de, 99% ee) (HPLC measurement conditions: Chiralcel OD-H column, n-hexane/isopropanol=98/2, 0.8 mL/min, λ=214 nm, t$_R$(large peak)=13.3 min, t$_R$(small peak)=15.8 min, t$_R$(small peak)=19.7 min, t$_R$(large peak)=22.4 min); $[\alpha]^{21}_D$=−61.9 (c=1.02, CHCl₃); ¹H NMR (300 MHz, CDCl₃) δ=7.39-7.21 (m, 5H, Ar—H), 5.47-5.39 (m, 1H, one proton from HC=C=CH), 5.37-5.29 (m, 1H, one proton from HC=C=CH), 5.21-5.14 (m, 1H, PhCH), 2.36 (d, J=3.0 Hz, 1H, OH), 2.07-1.93 (m, 1H, CH from Cy), 1.81-1.57 (m, 5H, protons from Cy), 1.35-0.97 (m, 5H, protons from Cy); ¹³C NMR (75 MHz, CDCl₃) δ=201.2, 200.9, 143.1, 143.0, 128.2, 127.45, 127.38, 126.1, 125.9, 101.0, 100.6, 96.93, 96.85, 72.3, 72.1, 37.04, 37.01, 32.8, 25.95, 25.85; MS (EI) m/z (%): 228 (M⁺, 3.11), 107 (100); IR (neat): v=3355, 2923, 2850, 1962, 1493, 1449, 1013 cm⁻¹.

Example 14

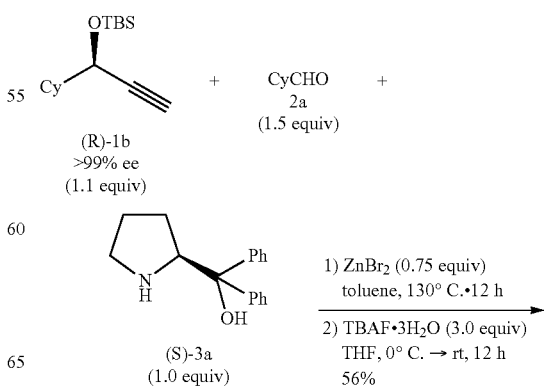

-continued

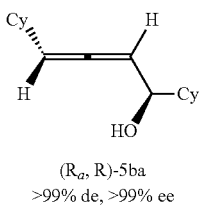

(R$_a$, R)-5ba
>99% de, >99% ee

Operations were conducted by referring to Example 1: Using ZnBr$_2$ (169.5 mg, 0.75 mmol), α, α-diphenylprolinol (S)-3a (258.3 mg, 1.0 mmol), propargyl alcohol protected by tert-butyldimethylsilyl group (R)-1b (277.9 mg, 1.1 mmol), newly distilled cyclohexanecarboxaldehyde 2a (168.4 mg, 1.5 mmol), dehydrated toluene (3 mL), TBAF·3H$_2$O (947.2 mg, 3.0 mmol) and tetrahydrofuran (3 mL), column chromatography (petroleum ether/ethyl acetate=25/1) to afford a liquid: axially chiral α-allenic alcohol (R$_e$, R)-5ba (131.8 mg, 56%): >99% de, >99% ee (HPLC measurement conditions: Chiralcel PC-2 column, n-hexane/isopropanol=98/2, 0.5 mL/min, λ=214 nm, t$_R$(small peak)=10.0 min, t$_R$(large peak)=11.4 min; [α]$^{21}_D$=−118.8 (c=1.03, CHCl$_3$); $^1$H NMR (300 MHz, CDCl$_3$) δ=5.28-5.15 (m, 2H, CH=C=CH), 3.84 (t, J=5.7 Hz, 1H, OCH), 2.04-1.54 (m, 12H, OH and protons from Cy), 1.46-0.90 (m, 11H, protons from Cy); $^{13}$C NMR (75 MHz, CDCl$_3$) δ=201.4, 99.7, 94.9, 74.5, 43.9, 37.1, 33.01, 32.96, 28.7, 28.3, 26.5, 26.1, 26.00, 25.97, 25.9; MS (EI) m/z (%): 234 (M$^+$, 1.93), 55 (100); IR (neat): ν=3373, 2922, 2851, 1960, 1448, 1083, 1008 cm$^{-1}$; HRMS [M$^+$] calculated value: 234.1984, measured value: 234.1985.

Example 15

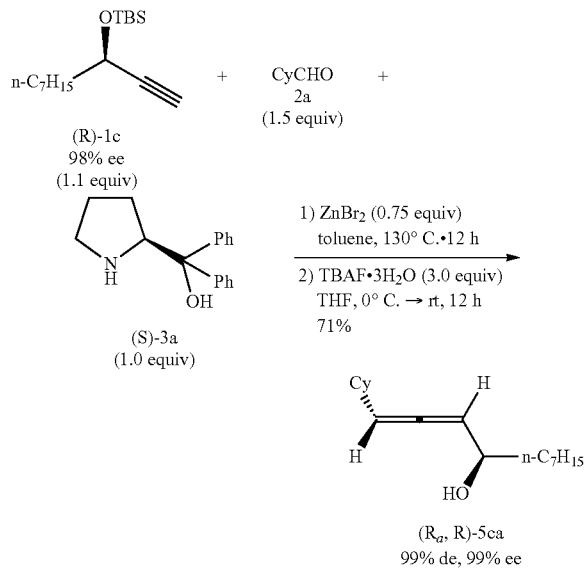

Operations were conducted by referring to Example 1: Using ZnBr$_2$ (169.7 mg, 0.75 mmol), α, α-diphenylprolinol (S)-3a (258.3 mg, 1.0 mmol), propargyl alcohol protected by tert-butyldimethylsilyl group (R)-1c (295.5 mg, 1.1 mmol), newly distilled cyclohexanecarboxaldehyde 2a (168.4 mg, 1.5 mmol), dehydrated toluene (3 mL), TBAF·3H$_2$O (947.2 mg, 3.0 mmol) and tetrahydrofuran (3 mL), column chromatography (petroleum ether/ethyl acetate=25/1) to afford a liquid: axially chiral α-allenic alcohol (R$_a$, R)-5ca (178.3 mg, 71%): 99% de, >99% ee (HPLC measurement conditions: Chiralcel IC column, n-hexane/isopropanol=100/1, 0.5 mL/min, λ=214 nm, t$_R$(small peak)=12.5 min, t$_R$(small peak)=13.1 min, t$_R$(large peak)=14.9 min; [α]$^{21}_D$=−80.8 (c=1.04, CHCl$_3$); $^1$H NMR (300 MHz, CDCl$_3$) λ=5.32-5.18 (m, 2H, CH=C=CH), 4.10 (d, J=6.0 Hz, 1H, OCH), 2.06-1.92 (m, 2H, OH and proton from Cy), 1.81-0.99 (m, 22H, protons from Cy and n-C$_7$H$_{15}$), 0.88 (t, J=6.6 Hz, 3H, CH$_3$); $^{13}$C NMR (75 MHz, CDCl$_3$) δ=201.1, 99.7, 96.5, 70.3, 37.4, 37.1, 33.01, 32.97, 31.7, 29.4, 29.2, 26.0, 25.9, 25.4, 22.6, 14.0; MS (EI) m/z (%): 250 (M$^+$, 0.56), 55 (100); IR (neat): ν=3345, 2923, 2852, 1962, 1448, 1047, 1017 cm$^{-1}$; HRMS [M$^+$] calculated value: 250.2297, measured value: 250.2296.

Example 16

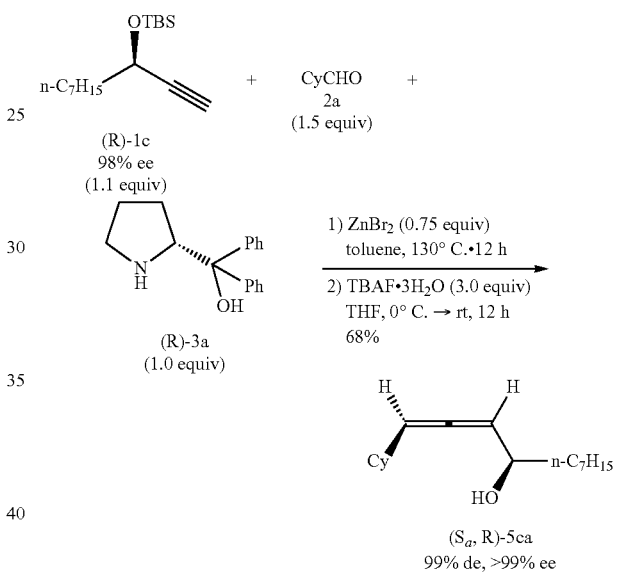

Operations were conducted by referring to Example 1: Using ZnBr$_2$ (169.7 mg, 0.75 mmol), α, α-diphenylprolinol (R)-3a (258.4 mg, 1.0 mmol), propargyl alcohol protected by tert-butyldimethylsilyl group (R)-1c (295.7 mg, 1.1 mmol), newly distilled cyclohexanecarboxaldehyde 2a (168.6 mg, 1.5 mmol), dehydrated toluene (3 mL), TBAF·3H$_2$O (947.2 mg, 3.0 mmol) and tetrahydrofuran (3 mL), column chromatography (petroleum ether/ethyl acetate=25/1) to afford a liquid: axially chiral α-allenic alcohol (S$_a$, R)-5ca (171.1 mg, 68%): 99% de, >99% ee (HPLC measurement conditions: Chiralcel IC column, n-hexane/isopropanol=100/1, 0.5 mL/min, λ=214 nm, t$_R$(large peak)=14.8 min, t$_R$(small peak)=17.6 min, t$_R$(small peak)=18.3 min; [α]$^{22}_D$=61.8 (c=1.07, CHCl$_3$); $^1$H NMR (300 MHz, CDCl$_3$) δ=5.33-5.18 (m, 2H, CH=C=CH), 4.10 (t, J=2.6 Hz, 1H, OCH), 2.07-1.93 (m, 1H, proton from Cy), 1.89 (s, 1H, OH), 1.82-1.00 (m, 22H, protons from Cy and n-C$_7$H$_{15}$), 0.88 (t, J=6.8 Hz, 3H, CH$_3$); $^{13}$C NMR (75 MHz, CDCl$_3$) δ=200.7, 100.1, 96.7, 69.7, 37.5, 37.0, 33.0, 32.9, 31.7, 29.4, 29.2, 26.0, 25.9, 25.4, 22.5, 13.9; MS (EI) m/z (%): 250 (M$^+$, 0.96), 55 (100); IR (neat): ν=3334, 2923, 2852, 1962, 1449, 1047, 1019 cm$^{-1}$; HRMS [M$^+$] calculated value: 250.2297, measured value: 250.2299.

Example 17

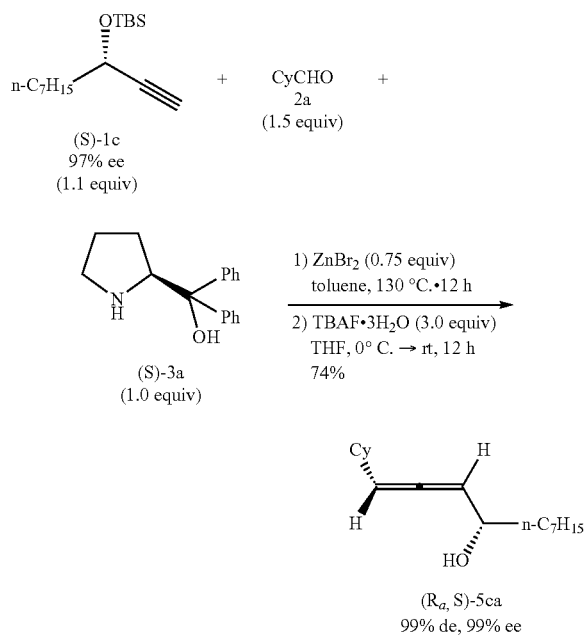

Operations were conducted by referring to Example 1: Using ZnBr$_2$ (169.6 mg, 0.75 mmol), α, α-diphenylprolinol (S)-3a (258.5 mg, 1.0 mmol), propargyl alcohol protected by tert-butyldimethylsilyl group (S)-1c (295.7 mg, 1.1 mmol), newly distilled cyclohexanecarboxaldehyde 2a (168.5 mg, 1.5 mmol), dehydrated toluene (3 mL), TBAF·3H$_2$O (947.4 mg, 3.0 mmol) and tetrahydrofuran (3 mL), column chromatography (petroleum ether/ethyl acetate=25/1) to afford a liquid: axially chiral α-allenic alcohol (R$_a$, S)-5ca (186.2 mg, 74%): 99% de, 99% ee (HPLC measurement conditions: Chiralcel IC column, n-hexane/isopropanol=100/1, 0.5 mL/min, λ=214 nm, t$_R$(small peak)=16.5 min, t$_R$(large peak)=17.9 min, t$_R$(small peak)=20.0 min, t$_R$(small peak)=20.9 min; [α]$^{20}_D$=−58.2 (c=1.04, CHCl$_3$); $^1$H NMR (300 MHz, CDCl$_3$) δ=5.32-5.18 (m, 2H, CH=C=CH), 4.09 (s, 1H, OCH), 2.07-1.90 (m, 2H, OH and proton from Cy), 1.82-1.00 (m, 22H, protons from Cy and n-C$_7$H$_{15}$), 0.88 (t, J=6.6 Hz, 3H, CH$_3$); $^{13}$C NMR (75 MHz, CDCl$_3$) δ=200.7, 100.2, 96.7, 69.7, 37.5, 37.1, 33.0, 32.9, 31.7, 29.5, 29.2, 26.0, 25.9, 25.4, 22.6, 14.0; MS (EI) m/z (%): 250 (M$^+$, 0.55), 55 (100); IR (neat): ν=3336, 2923, 2852, 1962, 1448, 1121, 1047, 1019 cm$^{-1}$; HRMS [M$^+$] calculated value: 250.2297, measured value: 250.2295.

Example 18

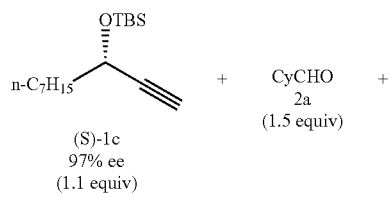

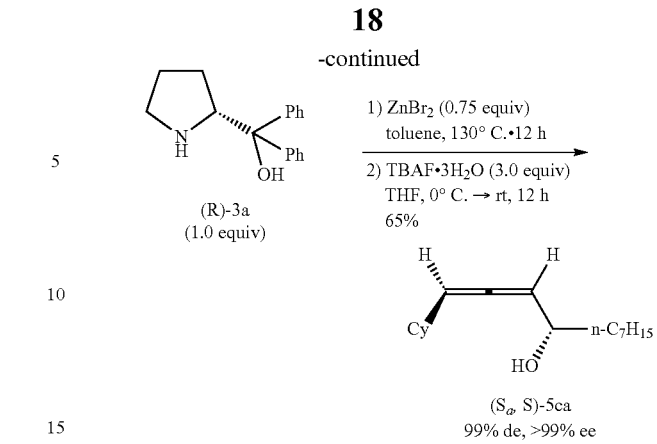

Operations were conducted by referring to Example 1: ZnBr$_2$ (169.4 mg, 0.75 mmol), α, α-diphenylprolinol (R)-3a (258.3 mg, 1.0 mmol), propargyl alcohol Using protected by tert-butyldimethylsilyl group (S)-1c (295.2 mg, 1.1 mmol), newly distilled cyclohexanecarboxaldehyde 2a (168.5 mg, 1.5 mmol), dehydrated toluene (3 mL), TBAF·3H$_2$O (947.2 mg, 3.0 mmol) and tetrahydrofuran (3 mL), column chromatography (petroleum ether/ethyl acetate=25/1) to afford a liquid: axially chiral α-allenic alcohol (S$_a$, S)-5ca (162.3 mg, 65%): 99% de, >99% ee (HPLC measurement conditions: Chiralcel IC column, n-hexane/isopropanol=100/1, 0.5 mL/min, λ=214 nm, t$_R$(small peak)=16.5 min, t$_R$(small peak)=17.5 min, t$_R$(small peak)=20.1 min, t$_R$(large peak)=21.0 min; [α]$^{20}_D$=79.4 (c=1.04, CHCl$_3$); $^1$H NMR (300 MHz, CDCl$_3$) δ=5.31-5.19 (m, 2H, CH=C=CH), 4.11 (d, J=6.0 Hz, 1H, OCH), 2.06-1.91 (m, 1H, proton from Cy), 1.88 (s, 1H, OH), 1.81-0.99 (m, 22H, protons from Cy and n-C$_7$H$_{15}$), 0.88 (t, J=6.6 Hz, 3H, CH$_3$); $^{13}$C NMR (75 MHz, CDCl$_3$) δ=201.1, 99.8, 96.6, 70.3, 37.5, 37.1, 33.03, 32.98, 31.8, 29.4, 29.2, 26.0, 25.9, 25.4, 22.6, 14.0; MS (EI) m/z (%): 250 (M$^+$, 0.71), 55 (100); IR (neat): ν=3343, 2923, 2852, 1962, 1448, 1120, 1048, 1020 cm$^{-1}$; HRMS [M$^+$] calculated value: 250.2297, measured value: 250.2303.

Example 19

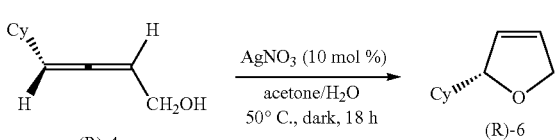

Axially chiral α-allenic alcohol (R)-4aa (76.2 mg, 0.5 mmol, 99% ee), acetone (3 mL) and 0.05 mol/l of AgNO$_3$ solution (1 mL, 0.05 mmol) were added in sequence to a dried reaction tube. The reaction tube was equipped with a reflux condensing tube, and was placed into an oil bath that had been previously heated to 50° C., and the resulting mixture was stirred for 18 hours. After cooling to room temperature, ethyl acetate (10 mL) and saturated saline solution (10 mL) were added to the reaction tube. The organic layer was separated, and the water layer was extracted with ethyl acetate (10 mL×3). And the organic layers were combined, washed with saturated saline solution (10 mL), dried with anhydrous sodium sulfate, evaporated, and subjected to column chromatography (petroleum ether/ether=40/1) to afford a liquid: compound (R)-6 (59.7 mg, 78%): 99% ee (HPLC measurement conditions: Chiralcel AD-H column, n-hexane/isopropanol=400/1, 0.5 mL/min, λ=214 nm, $t_R$(large peak)=10.2 min, $t_R$(small peak)=11.5 min); $[α]22_D$=−161.8 (c=1.05, CHCl$_3$); $^1$H NMR (300 MHz, CDCl$_3$) δ=5.90 (d, J=6.6 Hz, 1H, one proton from CH=CH), 5.79 (d, J=6.0 Hz, 1H, one proton from CH=CH), 4.60 (s, 3H, OCH and OCH$_2$), 1.83-1.59 (m, 5H, proton from Cy), 1.54-1.38 (m, 1H, proton from Cy), 1.32-0.90 (m, 5H, protons from Cy); $^{13}$C NMR (75 MHz, CDCl$_3$) δ=128.0, 126.7, 90.6, 75.2, 43.4, 28.6, 28.4, 26.5, 26.13, 26.10; MS (EI) m/z (%): 152 (M$^+$, 0.84), 69 (100); IR (neat): v=2924, 2851, 1449, 1350, 1083, 1068, 1021 cm$^{-1}$; HRMS [M$^+$] calculated value: 152.1201, measured value: 152.1202. (References: J. A. Mashall, X.-J. Wang, *J. Org. Chem.* 1991, 56, 4913; C. M. Sapu, J. E. Bäckvall, J. Deska, *Angew. Chem. Int. Ed.* 2011, 50, 9731)

Example 20

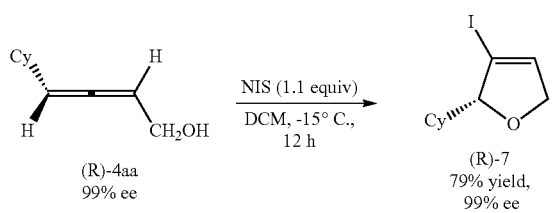

(R)-4aa
99% ee (R)-7
79% yield,
99% ee

Axially chiral α-allenic alcohol (R)-4aa (76.5 mg, 0.5 mmol, 99% ee) and 2 mL of dichloromethane were added in sequence to a dried reaction tube, and added with N-iodosuccinimide (124.0 mg, 0.55 mmol) and 1 mL of dichloromethane at −15° C.; after the addition, the resulting mixture was continuously stirred at −15° C. for 12 hours. After the reaction, Na$_2$S$_2$O$_3$ (10 mL) was added to quench the reaction. The organic layer was separated, and the water layer was extracted with dichloromethane (10 mL×3). The organic layers were combined, washed with saturated saline solution (10 mL), dried with anhydrous sodium sulfate, evaporated, and subjected to column chromatography (petroleum ether/ether=50/1) to afford a liquid compound (R)-7 (110.3 mg, 79%): 99% ee (HPLC measurement conditions: Chiralcel AD-H column, n-hexane/isopropanol=100/1, 0.3 mL/min, λ=214 nm, $t_R$(large peak)=12.3 min, $t_R$(small peak)=13.1 min); $[α]^{22}_D$=+6.0 (c=1.04, CHCl$_3$); $^1$H NMR (300 MHz, CDCl$_3$) δ=6.26 (s, 1H, C=CH), 4.66-4.44 (m, 3H, OCH and OCH$_2$), 1.83-1.57 (m, 5H, proton from Cy), 1.52-0.95 (m, 6H, protons from Cy); $^{13}$C NMR (75 MHz, CDCl$_3$) δ=135.1, 93.5, 91.0, 76.9, 40.6, 30.1, 26.7, 26.3, 26.0, 24.2; MS (EI) m/z (%): 278 (M$^+$, 11.82), 195 (100); IR (neat): v=2924, 2850, 1613, 1449, 1342, 1311, 1281, 1234, 1178, 1102, 1087, 1067, 1019 cm$^{-1}$; HRMS [M$^+$] calculated value: 278.0168, measured value: 278.0169. (References: C. J. T. Hyland, L. S. Hegedus, *J. Org. Chem.* 2006, 71, 8658; B. Lu, X. Jiang, C. Fu, S. Ma, *J. Org. Chem.* 2009, 74, 438; J. Deska, J. E. Bäckvall, *Org. Biomol. Chem.* 2009, 7, 3379)

Example 21

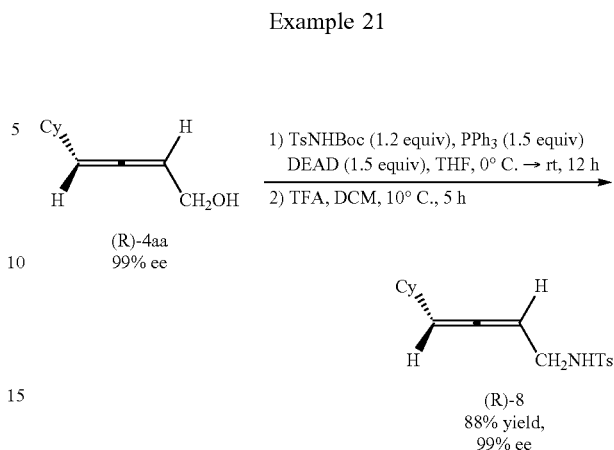

(R)-4aa
99% ee (R)-8
88% yield,
99% ee

Under the protection of an inert gas, triphenylphosphine (197.2 mg, 0.75 mmol), p-toluenesulphonamide protected by tert-butoxylcarbonyl group (163.0 mg, 0.6 mmol), axially chiral α-allenic alcohol (R)-4aa (76.3 mg, 0.5 mmol, 99% ee), and dehydrated tetrahydrofuran (2 mL) were added in sequence to a dried reaction tube. Diethyl azodicarboxylate (131.1 mg, 0.75 mmol) was then dissolved in 1 mL of dehydrated tetrahydrofuran and was added dropwise into the reaction system at 0° C. via an injector within 20 minutes. After the addition, the temperature was naturally increased to the room temperature and the reaction system was stirred for 12 hours. After reaction, the product was subjected to evaporation and column chromatography (petroleum ether/ethyl acetate/dichloromethane=15/1/0.1), an allenic amine protected by tert-butoxylcarbonyl group was obtained. The obtained allenic amine was then directly dissolved in 3 mL of dichloromethane, and 0.15 mL of trifluoroacetic acid was added at 10° C., the resulting mixture was stirred for 2.5 hours and followed by addition of 0.15 mL of trifluoroacetic acid, and then continuously stirred for 2.5 hours. After the reaction, the product was subjected to evaporation so as to remove most of trifluoroacetic acid, and then 10 mL of dichloromethane and 20 mL of saturated NaHCO$_3$ solution were added. Organic layer was separated, and the water layer was extracted with dichloromethane (10 mL×3). The organic layers were combined, washed with saturated saline solution (10 mL), dried with anhydrous sodium sulfate, evaporated, and subjected to column chromatography (petroleum ether/ethyl acetate=9/1) to afford a liquid compound (R)-8 (134.9 mg, 88%, total yield after two-step operation): 99% ee (HPLC measurement conditions: Chiralcel AD-H column, n-hexane/isopropanol=95/5, 0.5 mL/min, λ=214 nm, $t_R$(large peak)=36.3 min, $t_R$(small peak)=38.4 min); $[α]22_D$=−105.5 (c=1.07, CHCl$_3$); $^1$H NMR (300 MHz, CDCl$_3$) δ=7.77 (d, J=7.8 Hz, 2H, Ar—H), 7.30 (d, J=7.5 Hz, 2H, Ar—H), 5.21-5.12 (m, 1H, CH=C=CH), 5.11-5.01 (m, 1H, CH=C=CH), 4.92 (t, J=5.3 Hz, 1H, NH), 3.59-3.50 (m, 2H, NCH$_2$), 2.42 (s, 3H, CH$_3$), 1.98-1.83 (m, 1H, proton from Cy), 1.75-1.53 (m, 5H, protons from Cy), 1.33-0.89 (m, 5H, protons from Cy); $^{13}$C NMR (75 MHz, CDCl$_3$) δ=202.2, 143.2, 137.0, 129.5, 127.0, 100.3, 88.4, 42.0, 36.7, 32.8, 32.7, 25.9, 25.7, 21.4; MS (EI) m/z (%): 305 (M$^+$, 2.03), 55 (100); IR (neat): v=3280, 2923, 2850, 1963, 1598, 1447, 1421, 1325, 1158, 1093 cm$^{-1}$; HRMS [M$^+$] calculated value: 305.1450, measured value: 305.1451. (Reference: O. Mitsunobu, M. Yamada, *Bull. Chem. Soc. Jpn.* 1967, 40, 2380; O. Mitsunobu, *Synthesis* 1981, 1)

Example 22

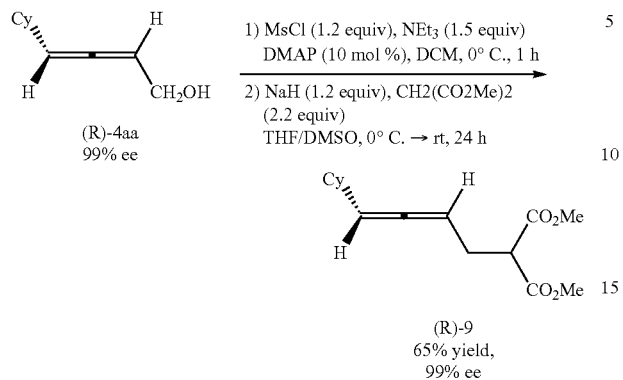

Under the protection of an inert gas, p-dimethylaminopyridine (6.2 mg, 0.05 mmol), dehydrated triethylamine (76.1 mg, 0.75 mmol), axially chiral α-allenic alcohol (R)-4aa (76.2 mg, 0.5 mmol, 99% ee), and dehydrated DCM (3 mL) were added in sequence to a reaction tube. Methanesulfonyl chloride (47 μl, d=1.475, 0.6 mmol) was added dropwise into the reaction system at 0° C. via an injector within 15 minutes, and the resulting mixture was further stirred at 0° C. for 1 hour after the addition. After the reaction, 10 mL of water and 10 mL of dichloromethane were added, the organic layer was separated, and the water layer was extracted with dichloromethane (10 mL×3), the resulting organic layers were combined and 2 g of smashed ice was added. The resulting mixture was washed in sequence with 1 M HCl (10 mL), saturated NaHCO$_3$ solution (10 mL) and saturated saline solution (10 mL); dried with anhydrous sodium sulfate, evaporated and directly used for the following reactions. In another reaction tube, sodium hydride (24.1 mg, 0.6 mmol, 60%) was added, and then dehydrated tetrahydrofuran (1 mL), dehydrated DMSO (0.25 mL), and dimethyl malonate (145.5 mg, 1.1 mmol) were added in sequence at 0° C., and the temperature was increased to room temperature after the additions, which was followed by stirring for 30 minutes The crude product obtained in the last step was dissolved in 1 mL of dehydrated tetrahydrofuran and was added dropwise via injector into the above reaction system within 30 minutes. After the addition, the resulting mixture was stirred for 24 hours at room temperature. After the reaction, 10 mL of saturated NH$_4$Cl was added at 0° C. so as to quench the reaction; and then 10 mL of ether was added. Organic layer was separated and the water layer was extracted with ether (10 mL×3). The resulting organic layers were combined, washed with saturated saline solution (10 mL), dried with anhydrous sodium sulfate, evaporated, and subjected to column chromatography (petroleum ether/ether=25/1) (87.1 mg, 65%, the total yield of two steps) to afford a liquid compound (R)-9: 99% ee (HPLC measurement conditions: Chiralcel OD-H column, n-hexane/isopropanol=100/1, 1 mL/min, λ=214 nm, $t_R$(small peak)=7.2 min, $t_R$(large peak)=7.9 min); $[\alpha]^{22}_D$=−85.4 (c=1.05, CHCl$_3$); $^1$H NMR (300 MHz, CDCl$_3$) δ=5.20-5.09 (m, 2H, CH=C=CH), 3.74 (s, 6H, two CH$_3$), 3.51 (t, J=7.2 Hz, 1H, CH), 2.64-2.52 (m, 2H, CH$_2$), 2.01-1.85 (m, 1H, proton from Cy), 1.79-1.58 (m, 5H, protons from Cy), 1.36-0.96 (m, 5H, protons from Cy); $^{13}$C NMR (75 MHz, CDCl$_3$) δ=202.7, 169.34, 169.29, 98.9, 88.2, 52.44, 52.42, 51.2, 37.1, 32.9, 32.8, 28.1, 26.0, 25.9; MS (EI) m/z (%): 266 (M$^+$, 19.00), 91 (100); IR (neat): ν=2924, 2851, 1962, 1736, 1437, 1342, 1262, 1231, 1150, 1035 cm$^{-1}$; HRMS [M$^+$] calculated value: 266.1518, measured value: 266.1516. (Reference: Z. Zhang, C. F. Bender, R. A. Widenhoefer, *J. Am. Chem. Soc.* 2007, 129, 14148).

What is claimed is:

1. A method for synthesizing an axially chiral α-allenic alcohol having the following structural formula:

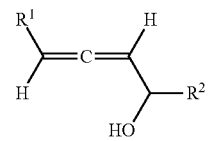

wherein R$^1$ is a C$_1$-C$_{10}$ hydrocarbon group; R$^2$ is H or C$_1$-C$_{10}$ hydrocarbon group; the axial chirality of the allene is in R or S configuration; the carbon atom linked to the hydroxyl group is non-chiral, or in R or S configuration; and when the C$_1$-C$_{10}$ hydrocarbon group is an aliphatic group, the ee value is higher than 96%, comprising the following steps:

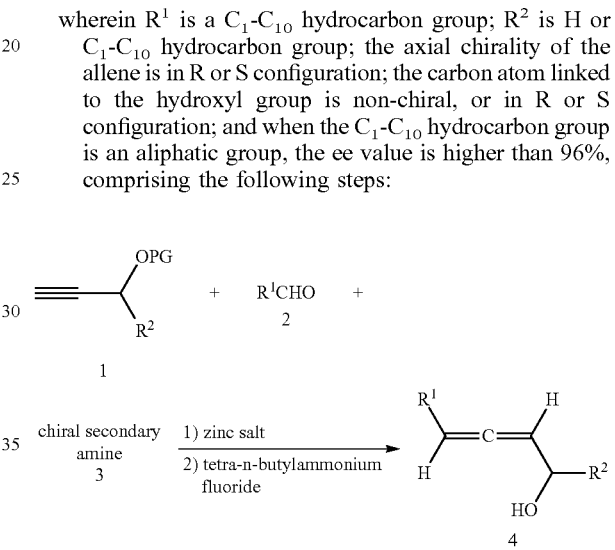

wherein PG is a silyl group;

said reaction is performed in an organic solvent and at a temperature of 100-130° C., in the presence of a zinc salt, and using (3) or an enantiomer thereof as a chiral secondary amine;

wherein the substituted-propargyl alcohol protected by silyl group (1) and the aldehyde (2) are reacted for 5-15 hours; followed by passing the protected product through a silica-gel chromatographic column to obtain a crude reaction product; and then removing the silyl protective group by treatment with tetra-n-butylammonium fluoride, to obtain the axially chiral α-allenic alcohol product (4);

wherein the molar ratio of the substituted-propargyl alcohol protected with the silyl group (1): the aldehyde (2): the chiral secondary amine (3): the zinc salt is 1-3:1-3:1:0.5-1.5;

wherein said silyl group is a trimethylsilyl, triisopropylsilyl, tert-butyldimethylsilyl, or tert-butyldiphenylsilyl group; said chiral secondary amine is compound 3(a-e) having the following structural formula or an enantiomer thereof;

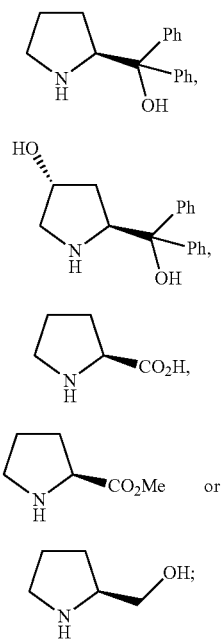

and wherein said zinc salt is zinc chloride, zinc bromide, zinc iodide, zinc acetate, or zinc trifluoromethanesulfonate.

2. The method of claim 1, wherein the zinc salt, chiral secondary amine, propargyl alcohol protected by silyl group, aldehyde, and dehydrated organic solvent are added to a dried reactor and stirred for 5-20 hours at 100-130° C.; and
after the reaction, the product is passed through a silica-gel chromatographic column to obtain a crude reaction product;
the crude reaction product is then dissolved in an organic solvent; and
the dissolved crude reaction product is mixed with tetra-n-butylammonium fluoride at 0° C. and stirred for 1-15 hours at room temperature.

3. The method of claim 1, wherein the organic solvent is benzene, toluene, chlorobenzene, p-xylene, o-xylene, m-xylene, or sym-trimethylbenzene.

4. The method of claim 1, wherein the deprotected axially chiral α-allenic alcohol reaction product is
washed with water,
extracted into an organic solvent,
dried,
subjected to evaporation of solvent; and
purified by column chromatographic separation.

5. The method of claim 2, wherein the organic solvent is benzene, toluene, chlorobenzene, p-xylene, o-xylene, m-xylene, or sym-trimethylbenzene.

6. The method of claim 2, wherein the deprotected axially chiral α-allenic alcohol reaction product is washed with water,
extracted into an organic solvent,
dried,
subjected to evaporation of solvent; and
purified by column chromatographic separation.

* * * * *